United States Patent [19]
Imura et al.

[11] Patent Number: 6,088,117
[45] Date of Patent: Jul. 11, 2000

[54] REFLECTION CHARACTERISTIC MEASURING APPARATUS

[75] Inventors: Kenji Imura, Toyohashi; Masayuki Makino, Aichi-ken; Wataru Yamaguchi, Toyokawa; Hiroshi Kohsaka; Naoki Sagisaka, both of Toyohashi, all of Japan

[73] Assignee: Minolta Co., Ltd., Osaka, Japan

[21] Appl. No.: 09/141,727

[22] Filed: Aug. 27, 1998

[30] Foreign Application Priority Data

Aug. 28, 1997 [JP] Japan .................................. 9-232721

[51] Int. Cl.⁷ .......................................... G01J 1/42
[52] U.S. Cl. .......................... 356/445; 356/236; 250/228
[58] Field of Search .................... 356/445, 446, 356/236; 250/228

[56] References Cited

U.S. PATENT DOCUMENTS

| 5,045,704 | 9/1991 | Coates | 356/445 |
| 5,384,641 | 1/1995 | Imura | |
| 5,859,709 | 1/1999 | Imura | 356/446 |

*Primary Examiner*—Frank G. Font
*Assistant Examiner*—Zandra Smith
*Attorney, Agent, or Firm*—McDermott, Will & Emery

[57] ABSTRACT

A reflection characteristic of a sample is measured using an integrating sphere by: measuring an apparent reflectance of a reference sample by using integrating sphere, the reference sample having a known true reflectance under a given illumination condition; calculating coefficients for rendering a linear combination of a measured apparent reflectance of the reference sample and N-th power (N is 2 or more integer) of the measured apparent reflectance closer to the known true reflectance of the reference sample; storing calculated coefficients in a storage medium as coefficients for the given illumination condition; measuring an apparent reflectance of a desired sample by using the integrating sphere; calculating a true reflectance of the desired sample under the given illumination condition by multiplying the terms of the linear combination of an measured apparent reflectance of the desired sample and N-th power of the measured apparent reflectance of the desired sample by the coefficients stored in the storage medium, respectively.

15 Claims, 5 Drawing Sheets

REFLECTION CHARACTERISTIC MEASURING APPARATUS

This application is based on patent application No. 9-232721 filed in Japan, the contents of which is hereby incorporated by reference.

BACKGROUND OF THE INVENTION

This invention relates to an apparatus for measuring a reflection characteristic of a sample using an integrating sphere, which may be adopted in a spectral colorimeter.

Generally, measurement of a reflectance of a sample is greatly affected by a configuration of an illuminator and a light receiving device (hereafter, referred to as "geometric configuration"). Accordingly, the Commission Internationale de l'Eclairage (CIE) recommends to use a reflection characteristic measuring apparatus with any one of the following geometric configurations as a reflection characteristic measuring apparatus such as a spectral calorimeter:

- 45/0: the illuminator is so arranged as to illuminate the sample surface with light incident upon the sample surface at 45°, and the light receiving device is so arranged as to receive light reflected from the sample surface at 90°;
- 0/45: the illuminator is so arranged as to illuminate the sample surface with light incident upon the sample surface at 90°, and the light receiving device is so arranged as to receive light reflected from the sample surface at 45°;
- d/0: the illuminator is so arranged as to illuminate the sample surface with diffused light, and the light receiving device is so arranged as to receive light reflected from the sample surface at 90°;
- 0/d: the illuminator is so arranged as to illuminate the sample surface with light incident upon the sample surface at 90°, and the light receiving device is so arranged as to receive diffused light.

Among the above configurations, d/8 type (combination of diffused-light-illuminator and +8°-inclined-light-receiving-device), a variation of the d/0 configuration, has been widely used because it can measure both a reflectance of a specular component included reflection light (or SCI spectral reflection) and a reflectance of a specular component excluded reflection light (or SCE spectral reflection). The SCI spectral reflection is unlikely to be influenced by the surface condition of the sample and hence has measurement reliability, and the SCE spectral reflection is close to visual sense.

However, there has been the problem residing in the conventional measuring apparatus that they lack the interchangeability of measurement data among apparatus even if the apparatus of the same geometric configuration are used. One reason for this is that despite the use of apparatus of the same geometric configuration, the apparatus do not coincide, in a strict meaning, with each other in terms of a spectral characteristic and a geometric configuration. It has been difficult to correct the reflectance in connection with wavelength and half bandwidth. It has been more difficult to make the geometric configuration of apparatus agree with each other with a high precision.

The measuring apparatus of d/8 configuration is incorporated with an integrating sphere for diffusely illuminating a sample. Even if the size of the integrating sphere used in the apparatus and the measurement area of the sample are identical, the illumination characteristic to the sample surface slightly differ from apparatus to apparatus. This is another hindrance against pursing the interchangeability of measurement data between apparatus.

Problems involved in pursuing the interchangeability of measurement data are described with reference to FIGS. 2A, 2B, and 3.

① Although an integrating sphere is adapted for diffusing light, the distribution of illumination light (hereafter, referred to as "light distribution") in integrating spheres differs from one another because their respective physical constructions and their respective reflective characteristics on inner surface are different from one another. Io in FIGS. 2A and 2B represents diffuse illumination light. The diffuse illumination light Io in FIG. 2A has a light distribution represented by a transversely expanded oval where light radiating in the −8° direction with respect to the normal line to a surface of a sample 3 is weak relative to other directions. On the other hand, the diffuse illumination light Io in FIG. 2B has a light distribution represented by a vertically expanded oval where light radiating in the −8° direction with respect to the normal line to the sample surface is strong relative to other directions. It is presumed that the total light amount of the diffuse illumination light Io in FIG. 2A is identical to that in FIG. 2B.

Figure 2A:
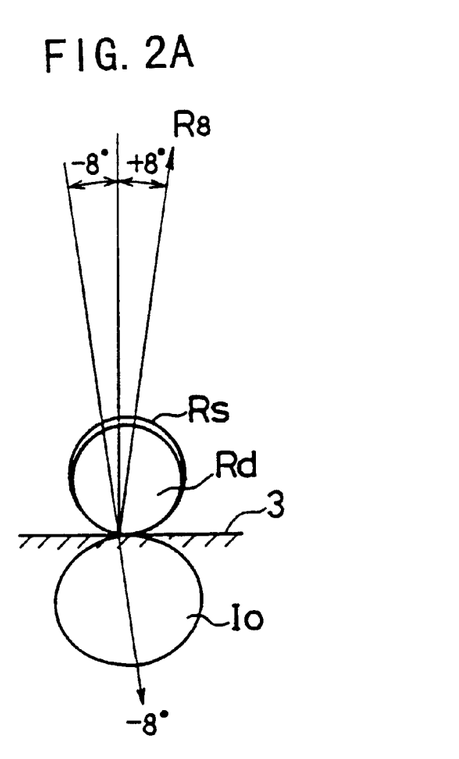
FIGS. 2A and 2B are diagrams showing a light distribution difference between measuring apparatus.
Figure 2B:
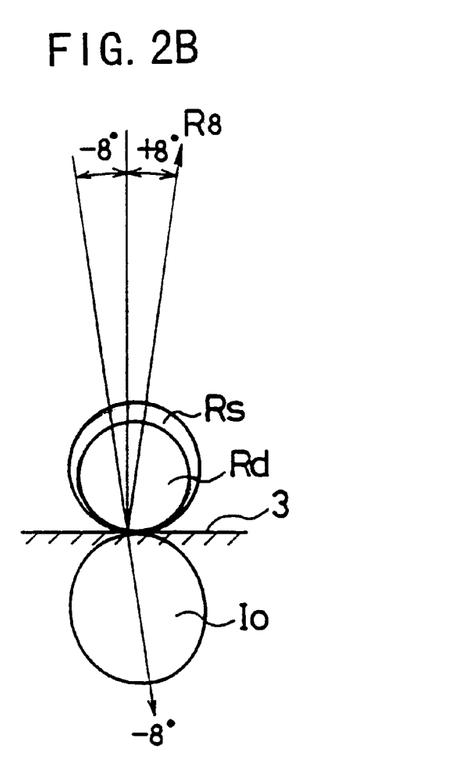

In the case where the sample has a luster surface in FIGS. 2A and 2B, light reflected from the sample 3 consists of diffuse reflection light Rd and specular reflection light Rs. The diffuse reflection light Rd is free from influence of the diffuse illumination light Io. Accordingly, it can be estimated that the light distribution and the light intensity of the diffuse reflection light Rd in FIG. 2A are identical to those in FIG. 2B. However, since the specular reflection light is subject to the light distribution of the diffuse illumination light Io, the specular reflection light Rs in FIG. 2B has stronger light in the +8 direction than that in FIG. 2A due to the light distribution of the diffuse illumination light Io in FIG. 2B.

Accordingly, what is observed on reflected light $R_8$ in the +8° direction in FIGS. 2A and 2B is that the light intensity of specular reflection light Rs, which does not show wavelength dependency or is free from the influence of wavelength, is strong relative to diffuse reflection light Rd, which exhibits wavelength dependency or is greatly affected by a wavelength peculiar to the sample, in FIG. 2B compared to in FIG. 2A. This causes a spectral reflectance difference between the samples in FIGS. 2A and 2B.

Figure 3:
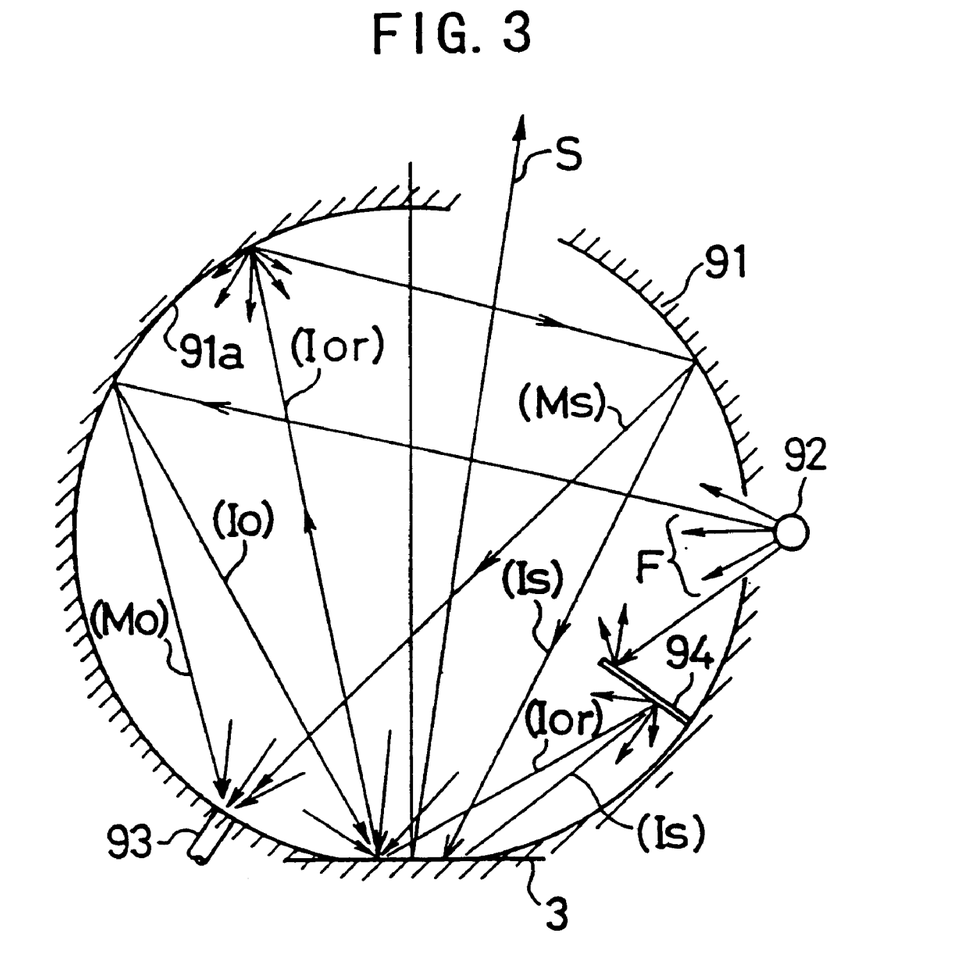
FIG. 3 is a diagram showing measurement error due to second illumination.

② Referring to FIG. 3, a beam of light F of a light source 92 is introduced in an integrating sphere 91 and undergoes a multiple reflection on an inner surface 91a of the integrating sphere 91. Part of diffuse light To illuminates a sample 3, and this light is reflected on the sample surface. Part of diffuse light Mo is incident on an optical fiber 93 as reference light or monitor light.

Since the sample 3 and an incident end of the optical fiber 93 are located at different positions, the diffuse lights Io and Mo have a certain proportional relationship (Io∞Mo) although not identical to each other. The proportional coefficient established between the diffuse lights Io and Mo varies merely depending on the geometric configuration of the integrating sphere.

Reflected light Ior which is reflected from the sample 3 is diffusely reflected on the inner surface 91a of the integrating sphere 91, and a part of the reflected light Ior illuminates the sample 3 again as diffuse light Is. In illuminating the sample 3 again, a part of the reflected light Ior is incident on the optical fiber 93 as reference diffuse light or monitor diffuse light Ms.

Hereafter, the diffuse lights Io and Mo are respectively referred to as "initial illumination light Io" and "initial monitor light Mo", whereas the diffuse lights Is and Ms are respectively referred to as "second illumination light Is" and "second monitor light Ms".

The second illumination light Is and the second monitor light Ms also have a certain proportional relationship which varies merely depending on the geometric configuration of the integrating sphere. In this time, however, the sample 3 itself becomes a light source for second illumination light. The sample 3 (or light source) is located at a position different from the light source 92. Consequently, the proportion coefficient established between the second illumination light Is and the second monitor light Ms is different from that between the initial sample light Io and the initial monitor light Mo. Further, the ratio of second illumination light to the whole illumination light varies in accordance with the reflectance of the sample 3. Accordingly, the illumination light cannot be accurately monitored or detected. The second illumination light proportionally rises with an increase in the reflectance (r) of a sample. Accordingly, measurement error due to variations in the reflectance is proportional to the square of the reflectance ($r^2$).

Figure 4:
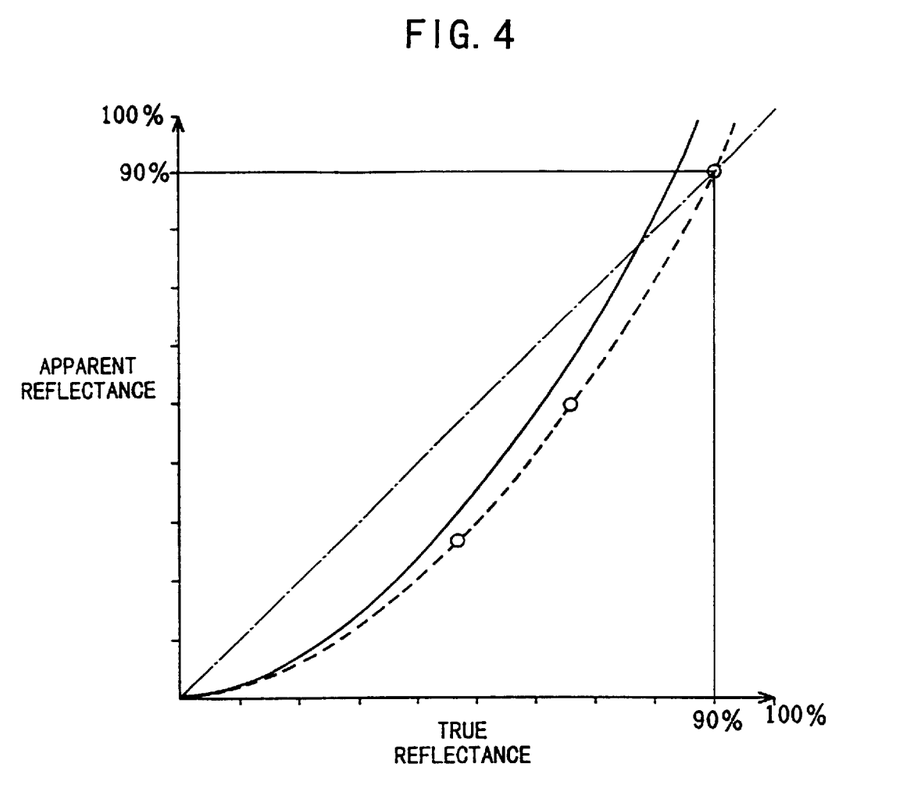
FIG. 4 is a diagram showing a calibration of a measuring apparatus using a white reference sample having a reflectance of 90%.

FIG. 4 shows calibration of a measuring apparatus with a white reference sample having a reflectance of 90% to correct such measurement error. In FIG. 4, the horizontal coordinate denotes a true reflectance of a sample and the vertical coordinate denotes an apparent reflectance or measured reflectance. The straight broken line represents an ideal state in which the true reflectance and the apparent reflectance match with one-to-one correspondence. The solid curve represents actual measurement results outputted from the measuring apparatus under the influence of second illumination light. The dashed curve represents calibrated results. As shown in FIG. 4, the calibrated curve is shifted down compared with the apparent reflectance. Accordingly, it will be seen that there is a likelihood that a calibrated measurement is lower than the true reflectance.

The measurement error due to second illumination is also caused by the structure in the vicinity of an aperture for a sample. As shown in FIG. 3, generally, an integrating sphere is provided with a buffer plate 94 near the sample aperture to prevent the sample 3 from being directly illuminated by the light from the light source 92. In this case, it is highly likely that light reflected from the sample 3 is reflected by the buffer plate 94 which in turn re-illuminates the sample 3. The position and the size of the buffer plate 94 is liable to differ from one integrating sphere to another. This difference is another cause for measurement error despite the use of measuring apparatus of the same type. Measurement error due to the difference in the position and size of buffer plate rises in proportion to the square of reflectance of a sample.

Figure 5:
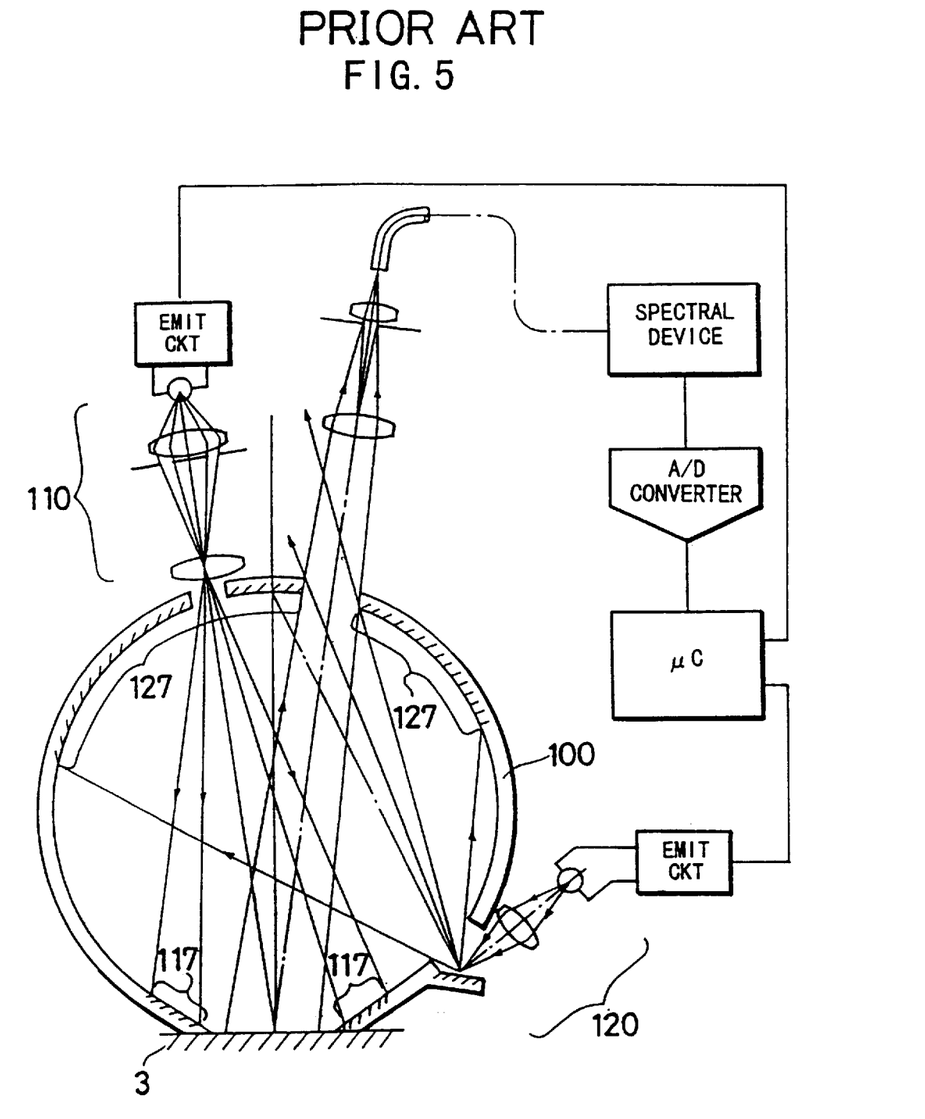
FIG. 5 is a diagram showing a construction of a conventional reflection characteristic measuring apparatus.

U.S. Pat. No. 5,384,641 discloses a measuring apparatus, as shown in FIG. 5, to correct the measurement error due to light distribution difference mentioned in the section ①. In FIG. 5, this measuring apparatus uses an integrating sphere 100 with illuminators 110, 120. The respective illuminators 110, 120 illuminate one after another illumination zones 117, 127 defined in different areas on an inner surface of the integrating sphere 100. The diffuse light distributions of the illuminators 110, 120 differ from each other.

The diffuse illumination light from the illuminators 110, 120 individually illuminates the sample 3, and obtained measurements are properly weighted and linearly combined so as to provide a reflectance approximate to a reflectance under a predetermined light distribution. This is performed to eliminate the measurement error due to light distribution difference pointed out in the section ①. However, this measuring apparatus cannot eliminate the measurement error due to second illumination which is pointed out in the section ②.

SUMMARY OF THE INVENTION

It is an object of the present invention to provide a reflection characteristic measuring apparatus and a reflection characteristic measuring method which have overcome the problems residing in the prior art.

According to an aspect of the present invention, a reflection characteristic measuring apparatus comprises: an integrating sphere formed with an illumination aperture, a sample aperture, and a reception aperture; an illuminator which supplies illumination light into the integrating sphere through the illumination aperture; a light receptor which receives light reflected from a sample placed at the sample aperture through the reception aperture to generate light reception data; an apparent reflectance calculator which calculates an apparent reflectance of the sample based on the generated light reception data; a storage unit which stores coefficients for rendering a linear combination of an apparent reflectance and N-th power (N is 2 or more integer) of the apparent reflectance closer to a true reflectance of the sample under a given illumination condition; and a true reflectance calculator which calculates a true reflectance of the sample under the given illumination condition by multiplying the terms of the linear combination of an apparent reflectance and N-th power (N is 2 or more integer) of the apparent reflectance by the coefficients stored in the storage unit, respectively.

According to another aspect of the present invention, a reflection characteristic measuring apparatus comprises: an integrating sphere formed with a first illumination aperture, a second illumination aperture, a sample aperture, and a reception aperture; a first illuminator which is provided at the first illumination aperture, and supplies a first kind of illumination light into the integrating sphere; a second illuminator which is provided at the second illumination aperture, and supplies a second kind of illumination light into the integrating sphere, the second kind of illumination light having a different light distribution from the first kind of illumination light; a light receptor which receives light reflected from a sample placed at the sample aperture through the reception aperture to generate light reception data; an apparent reflectance calculator calculates a first apparent reflectance of the sample under the first kind of illumination light and a second apparent reflectance of the sample under the second kind of illumination light; a storage unit which stores a plurality of predetermined weighting factors; and a true reflectance calculator which calculates a true reflectance of the sample under a given illumination condition by multiplying each of the first apparent reflectance, the second apparent reflectance, N-th power (N is 2 or more integer) of the first apparent reflectance, and N-th power (N is 2 or more integer) of the second apparent reflectance by their corresponding weighting factors stored in the storage unit, and adding their respective products to one another.

According to still another aspect of the present invention, a method for measuring a reflection characteristic of a sample using an integrating sphere, the method comprises the steps: measuring an apparent reflectance of a reference sample by using integrating sphere, the reference sample having a known true reflectance under a given illumination condition; calculating coefficients for rendering a linear combination of a measured apparent reflectance of the reference sample and N-th power (N is 2 or more integer) of the measured apparent reflectance closer to the known true reflectance of the reference sample; storing calculated coefficients in a storage medium as coefficients for the given illumination condition; measuring an apparent reflectance of a desired sample by using the integrating sphere; calculating a true reflectance of the desired sample under the given illumination condition by multiplying the terms of the linear combination of an measured apparent reflectance of the desired sample and N-th power (N is 2 or more integer) of the measured apparent reflectance of the desired sample by the coefficients stored in the storage medium, respectively.

According to yet still another aspect of the present invention, a method for measuring a reflection characteristic of a sample using an integrating sphere, the method comprises the steps: measuring a first apparent reflectance and a second apparent reflectance of a reference sample by using integrating sphere, the reference sample having a known true first reflectance and a known true second reflectance under a given illumination condition, the first apparent reflectance being measured under a first kind of illumination light, and the second apparent reflectance being measured under a second kind of illumination light; calculating coefficients for rendering a linear combination of a measured first apparent reflectance of the reference sample, N-th power (N is 2 or more integer) of the measured first apparent reflectance of the reference sample, a measured second apparent reflectance of the reference sample, and N-th power (N is 2 or more integer) of the measured second apparent reflectance of the reference sample closer to the known true reflectance of the reference sample; storing calculated coefficients in a storage medium as weighting factors for the given illumination condition; measuring a first apparent reflectance and a second apparent reflectance of a desired sample by using the integrating sphere, the first apparent reflectance being measured under the first kind of illumination light, and the second apparent reflectance being measured under the second kind of illumination light; calculating a true reflectance of the desired sample under the given illumination condition by multiplying the terms of the linear combination of a measured first apparent reflectance of the desired sample, N-th power (N is 2 or more integer) of the measured first apparent reflectance of the desired sample, a measured second apparent reflectance of the desired sample, and N-th power (N is 2 or more integer) of the measured second apparent reflectance of the desired sample by the weighting factors stored in the storage medium, respectively.

These and other objects, features and advantages of the present invention will become more apparent upon a reading of the following detailed description and accompanying drawings.

DETAILED DESCRIPTION OF THE PREFERRED EMBODIMENT OF THE INVENTION

Figure 1:
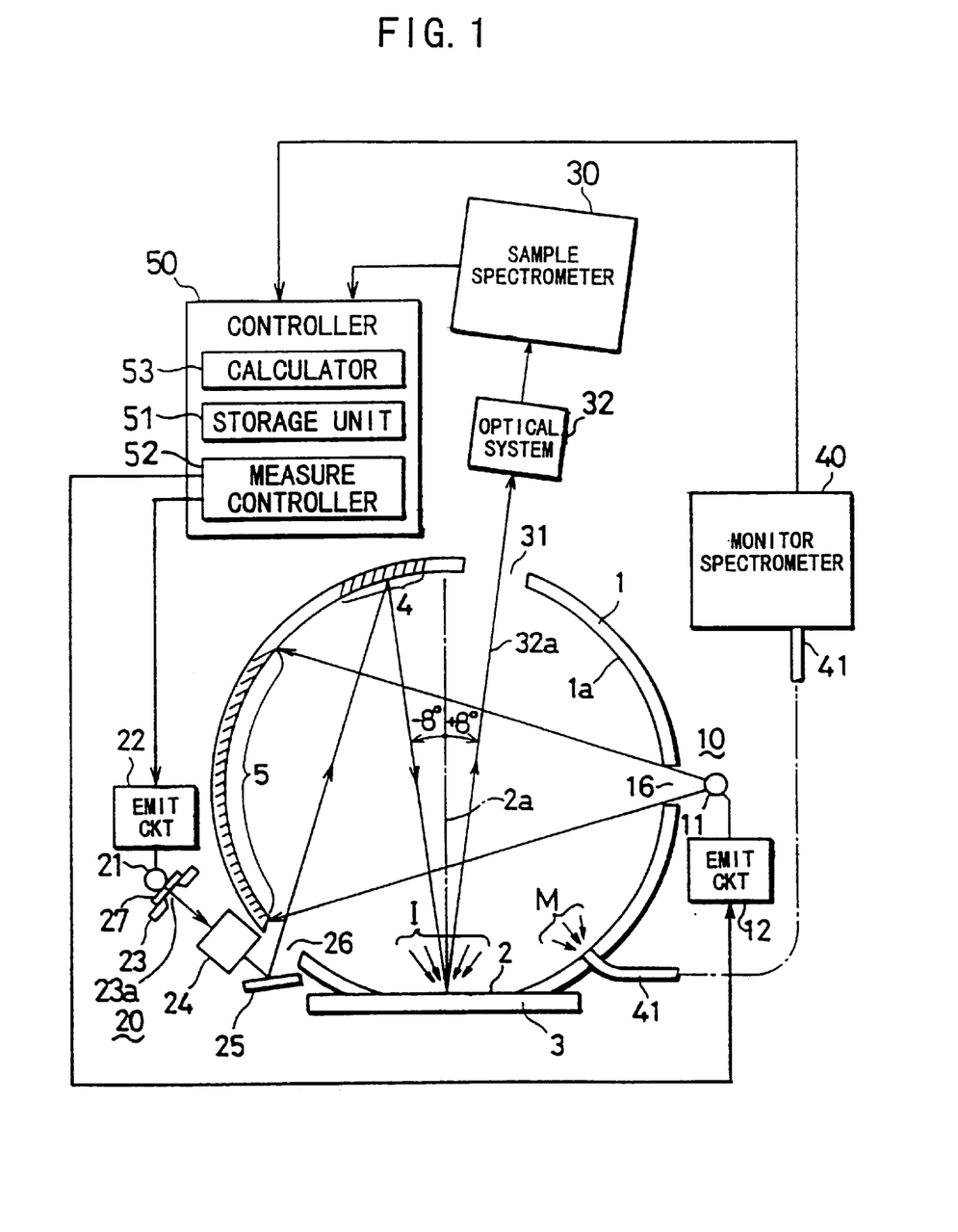
FIG. 1 is a diagram showing a construction of a reflection characteristic measuring apparatus embodying the present invention.

FIG. 1 shows a construction of a reflection characteristic measuring apparatus embodying the invention. This reflection characteristic measuring apparatus includes an integrating sphere 1. The integrating sphere 1 has a hollow sphere. An inner surface 1a of the integrating sphere 1 is applied with a white diffuse reflection paint, such as MgO and $BaSO_4$, having a high diffusion coefficient and a high reflection coefficient. The integrating sphere 1 is formed with a sample aperture 2 where a sample 3 to be measured is placed, a first light source aperture 16 for allowing light to be incident from a first illuminating system 10, a second light source aperture 26 for allowing light to be incident from a second illuminating system 20, and a measurement aperture 31 for allowing reflected light from the sample 3 to be incident upon a receiving optical system 32. The sample aperture 2 is formed in a bottom of the integrating sphere 1. The first light source aperture 16 is formed substantially at a center of a side portion of the integrating sphere 1. The second light source aperture 26 is formed in a left side portion to the sample aperture 2 in FIG. 1. The receiving optical system 32 is arranged on a path inclined by +8° with respect to a normal axis 2a to a surface of the sample 3.

The first illuminating system 10 includes a light source 11 and an emitting circuit 12 disposed in the vicinity of the integrating sphere 1. A xenon flash lamp or the like is used as the light source 11 to supply light into the integrating sphere 1 so as to first illuminate a direct illuminating region (or first region) 5 with a relatively large area in the inner surface 1a. The emitting circuit 12 drives the light source 11 to emit light, and is controlled by a measurement controller 52 which is described later.

The second illuminating system 20 includes a light source 21, an emitting circuit 22, an illumination region restricting plate 23, a converging member 24, and a reflector 25. A xenon flash lamp or the like is used as the light source 21 to supply light into the integrating sphere 1. The emitting circuit 22 drives the light source 21 to emit light, and is also controlled by the measurement controller 52.

The reflector 27 is disposed near the light source 21 and includes a translucent plate for diffusing the light from the light source 21. The restricting plate 23 has an aperture 23a and is adapted to restrict the illumination region of the light from the light source 21. The converging member 24 includes a lens, and is adapted to converge light passed through the aperture 23a on a direct illuminating region (or second region) 4 in the inner surface 1a via the reflector 25. The second region 4 is located along a direction of −8° with respect to the normal axis 2a. The second illuminating system 20 is arranged at such a position as to render the second region 4 and the measurement aperture 31 symmetrical with respect to the normal axis 2a.

The receiving optical system 32 includes a lens, and forms a d/8 optical system which is set such that an optical axis 32a is inclined by +8° with respect to the normal axis 2a of the surface of the sample 3. Hence, this optical system 32 receives a reflection light along the direction of +8° from the sample 3. The optical system 32 focuses the received reflection light on a sample spectrometer 30. The sample spectrometer 30 receives the reflection light from the sample 3 to output spectral data of the reflected light. The spectral data is transmitted to a controller 50 which is described later.

In the above arrangement, when the light source 11 of the first illuminating system 10 is turned on, light is projected onto the first region 5 of the inner surface 1a of the integrating sphere 1. The first region 5 has a large area, and the projected light undergoes a multiple reflection on the inner surface 1a. Accordingly, the sample 3 is substantially uniformly and diffusely illuminated from every direction by the first illuminating system 10.

When the light source 21 of the second illuminating system 20 is turned on, light from the light source 21 is limitedly projected to the second region 4 of the inner surface 1a of the integrating sphere 1. After reflected on the second region 4, the light also undergoes a multiple reflection. However, a certain part of the reflected light directly illuminates the sample 3, and light rays of specular reflection on the sample surface is incident on the light receiving system 32 through the measurement aperture 31. This means that the second illuminating system 20 resultantly illuminates the sample 3 with illumination light having such a light distribution that a strong specular reflection is added to the diffuse illumination light.

A light guide 41 is mounted on the integrating sphere 1. The light guide 41 includes an optical fiber or the like material, and introduces part of the illumination light in the integrating sphere 1, which is incident upon an incident end, to a monitoring spectrometer 40. The monitoring spectrometer 40 receives the illumination light to output spectral data of the illumination light. The spectral data is transmitted to the controller 50.

The controller 50 includes a CPU which centrally controls an operation of the reflection characteristic measuring apparatus. The controller 50 further comprises a storage unit 51, the measurement controller 52, and a calculator 53.

The storage unit 51 stores a control program for measurement and weighting factors set in advance, and temporarily stores the spectral data which is outputted from the sample spectrometer 30 and the monitoring spectrometer 40. The weighting factors are described later in detail.

The measurement controller 52 controls the emitting circuits 12, 22 to individually drive the light sources 11, 21 to emit light, while controlling the sample spectrometer 30 and the monitoring spectrometer 40 to output spectral data of the light emitted from the light sources 11, 21.

The calculator 53 calculates, according to a procedure which is described later, a reflectance of the sample 3 based on the respective spectral data and the weighting factors stored in the storage unit 51.

Next, measurement principle in the reflection characteristic measuring apparatus is described with reference to FIG. 1.

In FIG. 1, it is assumed that when no sample is placed on the sample aperture 2, the intensity of illumination light rays incident in the sample aperture 2 is $I_0$ and the intensity of illumination light rays incident onto the end of the optical fiber 41 is M. Also, it is assumed that when a sample 3 is placed on the sample aperture 2, the intensity of illumination light rays incident onto the sample 3 is I and the intensity of illumination light rays incident onto the end of the optical fiber 41 is M. The following Equation (1) can be established.

$$a = I_0/M_0 \quad \text{[Equation 1]}$$

where $a$ denotes the non-uniformity of diffuse illumination light.

Assuming that the true reflectance of the sample 3 is r, the intensities I and M are calculated in accordance with Equations (2) and (3) taking into account the second illumination of reflected light from the sample 3.

$$I = I_0 + I_0 \cdot r \cdot s_1 \quad \text{[Equation 2]}$$
$$= I_0(1 + r \cdot s_1)$$

$$M = M_0 + I_0 \cdot r \cdot s_2 \quad \text{[Equation 3]}$$
$$= M_0(1 + I_0/M_0 \cdot r \cdot s_2)$$

where $s_1$, $s_2$ are factors (or second illumination factors) influential to the reflectance r when the sample 3 and the incident end of the optical fiber 41 are re-illuminated by the reflected light of $I_0 \cdot r$ from the sample 3. The values $s_1$ and $s_2$ are usually very small.

Assuming that an apparent intensity of reflected light from the sample 3 is S, an apparent reflectance R of the reflected light can be expressed as: R=S/M.

I/M is calculated in accordance with Equation (5) based on Equations (1) to (3):

$$I/M = I_0(1 + r \cdot s_1)/\{M_0(1 + I_0/M_0 \cdot r \cdot s_2)\} \quad \text{[Equation 5]}$$
$$= a(1 + r \cdot s_1)/(1 + a \cdot r \cdot s_2)$$
$$\approx a(1 + r \cdot s_1)/(1 - a \cdot r \cdot s_2)$$
$$\approx a\{1 + r(s_1 - a \cdot s_2)\}$$
$$= a\{1 + b \cdot r\}$$

where $b=(s_1-a \cdot s_2)<<1$ and denotes the non-uniformity of second illumination originated from reflected light from the sample 3.

The illumination light intensity I is calculated in accordance with Equation (6).

$$I = a(1 + b \cdot r) \cdot M \quad \text{[Equation 6]}$$

The reflectance r of the sample 3 is calculated in accordance with Equation (7).

$$r = k \cdot S/I \quad \text{[Equation 7]}$$
$$= k \cdot S/\{a(1 + b \cdot r) \cdot M\}$$
$$\approx k \cdot R \cdot c(1 - b \cdot r)$$
$$\approx k \cdot R \cdot c(1 - b \cdot R)$$
$$= k \cdot (x \cdot R + y \cdot R^2)$$

where x=c=1/a, y=−(b·c)

In Equation (7), k is a calibration coefficient and is determined according to the following procedure. First, prior to measurement of the reflectance of the sample 3, using a white reference sample having a predetermined reference reflectance, the calibration coefficient k is so determined as to match an apparent reflectance R with the predetermined reference reflectance r. The calibration coefficient k is used to correct measurement error due to change in the geometric configuration of the reflection characteristic measuring apparatus.

As shown in Equation (7), the true reflectance r of the sample 3 can be expressed as a linear combination of an apparent reflectance R and the square of the apparent reflectance $R^2$, i.e., $r=k \cdot (x \cdot R+y \cdot R^2)$, where x denotes a weighting factor for R, and y denotes a weighting factor for $R^2$.

However, the relationship between the true reflectance r and the apparent reflectance R is not perfectly linear. The equation $r=k \cdot (x \cdot R+y \cdot R^2)$ includes the square term $(y \cdot R^2)$ having the insignificant weighting factor y. This square term represents the influence of second illumination originated from the reflected light from the sample 3.

The influence of second illumination is represented by the square term $(y \cdot R^2)$. Alternatively, this influence may be represented by the cubic term ($R^3$) or the term $R^N$ (N is the natural number more than 3). As a general expression, the term representing the influence of second illumination may be preferably represented by the expression $R^N$ (N is a natural number more than 1).

In measurement of the measuring apparatus shown in FIG. 1, the following Equation (8) is obtained. In Equation (8), $R_1$ denotes an apparent reflectance when the first illuminating system 10 is driven. $R_2$ denotes an apparent reflectance when the second illuminating system 20 is driven.

$$r_1 = p_1 \cdot R_1 + q_1 \cdot R_1^2$$
$$r_2 = p_2 \cdot R_2 + q_2 \cdot R_2^2 \qquad \text{[Equation 8]}$$

where $p_1$, $q_1$, and $p_2$, $q_2$ are respectively coefficients for the first illuminating system 10 and the second illuminating system 20, and $r_1$, $r_2$ are reflectances based on the first illuminating system 10 and the second illuminating system 20, respectively.

A true reflectance r of the sample 3 can be expressed as Equation (9) using appropriate weighting factors A and B.

$$r = k \cdot (A \cdot r_1 + B \cdot r_2) \qquad \text{[Equation 9]}$$
$$= k \cdot (g_1 \cdot R_1 + h_1 \cdot R_1^2 + g_2 \cdot R_2 + h_2 \cdot R_2^2)$$

where $g_1 = A \cdot p_1$, $h_1 = A \cdot q_1$, $g_2 = B \cdot p_2$, $h_2 = B \cdot q_2$.

Setting appropriate values as the coefficients $g_1$, $h_1$, and $g_2$, $h_2$, a true reflectance r of the sample 3 will be obtained under a given illumination condition.

Next, a measurement procedure for the measuring apparatus is described.

The measurement controller 52 is first activated to drive the emitting circuit 12 to render the light source 11 emit light to diffusely illuminate the sample 3 placed in the sample aperture 2 of the integrating sphere 1.

Subsequently, spectral data $S_1(\lambda)$ of reflected light from the sample 3 is outputted from the sample spectrometer 30 to the calculator 53, and spectral data $M_1(\lambda)$ of illumination light in the integrating sphere 1 is outputted from the monitoring spectrometer 40 to the calculator 53. It should be noted that, hereafter, the term ($\lambda$) for each data is omitted for the sake of simple explanation.

The calculator 53 calculates a first apparent reflectance $R_1$ in accordance with Equation (10) based on the obtained data.

$$R_1 = S_1 / M_1 \qquad \text{[Equation 10]}$$

Next, the measurement controller 52 is activated to drive the emitting circuit 22 to render the light source 21 emit light to illuminate the sample 3 with an intensive illumination light beam in the direction of −8°. A second apparent reflectance $R_2$ is calculated in accordance with Equation (11) in a similar manner as the first apparent reflectance $R_1$.

$$R_2 = S_2 / M_2 \qquad \text{[Equation 11]}$$

Subsequently, a true reflectance r of the sample 3 under a given illumination condition is calculated in accordance with Equation (12) with use of first weighting factors $g_1$, $h_1$, for the first illuminating system 10, second weighting factors $g_2$, $h_2$ for the second illuminating system 20, and calibration coefficient k which are all stored in the storage unit 51. The first weighting factors $g_1$, $h_1$ and the second weighting factors $g_2$, $h_2$ for the given illumination condition are calculated in advance and stored in the storage unit 51.

$$r = k \cdot (g_1 \cdot R_1 + h_1 \cdot R_1^2 + g_2 \cdot R_2 + h_2 \cdot R_2^2) \qquad \text{[Equation 12]}$$

As expressed by Equation (12), the true reflectance r of the sample 3 is a sum of the linear combination of the first apparent reflectance and the square of the first apparent reflectance ($g_1 \cdot R_1 + h_1 \cdot R_1^2$) and the linear combination of the second apparent reflectance and the square of the second apparent reflectance ($g_2 \cdot R_2 + h_2 \cdot R_2^2$).

It should be noted that in Equation (12), the weighting factor for the first apparent reflectance $R_1$ is $g_1$, the weighting factor for the square of the first apparent reflectance $R_1^2$ is $h_1$, the weighting factor for the second apparent reflectance $R_2$ is $g_2$, and the weighting factor for the square of the second apparent reflectance $R_2^2$ is $h_2$.

Next, described is determination of the first weighting factors $g_1$, $h_1$ and the second weighting factors $g_2$, $h_2$ for a given illumination condition.

The first weighting factors $g_1$, $h_1$ and the second weighting factors $g_2$, $h_2$ change with a variety of integrating sphere construction or others. In this embodiment, six reference samples SP1 to SP6 are used as reference samples. The six reference samples SP1 to SP6 are samples of achromatic color among which three have a luster surface and the other three have a mat surface. Each of the luster samples (mat samples) has a different luminosity. The respective reference reflectances $r_1$ to $r_6$ of the reference samples SP1 to SP6 are obtained and known in advance for each of a variety of illumination conditions.

First, the reference sample SP1 is placed in the sample aperture 2 to obtain a first apparent reflectance $R_{11}$ by the first illuminating system 10 and a second apparent reflectance $R_{21}$ by the second illuminating system 20. Subsequently, measurement is conducted with respect to the remaining reference samples SP2 to SP6 to obtain first apparent reflectances $R_{12}$ to $R_{16}$ by the first illuminating system 10 and second apparent reflectances $R_{22}$ to $R_{26}$ by the second illuminating system 20.

Based on results of these measurements or apparent first and second reflectances $R_{1i}$, $R_{2i}$, the following Equation (12) can be made:

$$e_i = r_i - (g_1 \cdot R_{1i} + h_1 \cdot R_{1i}^2 + g_2 \cdot R_{2i} + h_2 \cdot R_{2i}^2) \qquad \text{[Equation 13]}$$

wherein $e_i$ denotes a difference between a known reference reflectance $r_i$ for the given illumination condition and a true reflectance to be calculated by actually measured reflectances $R_{1i}$, $R_{2i}$ and first and second weighting factors $g_1$, $h_1$, $g_2$, $h_2$ which are to be calculated, and i is an integer from 1 to 6.

Optimal first weighting factors $g_1$, $h_1$ and second weighting factors $g_2$, $h_2$ are determined by the method of least squares about Equation (14).

$$T = (e_1)^2 + (e_2)^2 + (e_3)^2 + (e_4)^2 + (e_5)^2 + (e_6)^2 \qquad \text{[Equation 14]}$$

In this way, the optimal weighting factors $g_1$, $h_1$, $g_2$, $h_2$ for the given illumination condition are determined in advance and stored in the storage unit 51. The same procedure is performed to calculate weighting factors $g_1$, $h_1$, $g_2$, $h_2$ for each of the other illumination conditions.

The following illumination conditions may be applicable:

An illumination condition where no second illumination of reflected light from the sample occurs, and hence the distribution of illumination light is supposed to be uniform, namely approximate to an ideal state; and An illumination condition where peculiar second illumination originated from reflected light from a sample occurs and the distribution of illumination light is not uniform, and which is adoptable for a particular apparatus.

In the above description, the term (λ) is omitted for simplification of description. However, the reflectance, spectral data of received light, and illumination characteristics all vary in accordance with the wavelength. Accordingly, the first weighting factors and second weighting factors depend on the wavelength. In view thereof, it may be appreciated to provide weighting factors in accordance with the wavelength as weighting factors $g_1(\lambda)$, $h_1(\lambda)$, $g_2(\lambda)$, $h_2(\lambda)$.

In this embodiment, there are the first illuminating system 10 and the second illuminating system 20, which illuminate a sample with different light distributions. A true reflectance r of the sample under a given illumination condition is calculated in accordance with Equation (12) using first weighting factors $g_1$, $h_1$, second weighting factors $g_2$, $h_2$, which are determined for the given illumination condition and stored in the storage unit in advance, and calibration coefficient k. Accordingly, a true reflectance r under a given illumination condition can be obtained easily, which thus assures measurement data having a high data interchangeability.

The present invention is applicable to the following modifications (1) to (5).

(1) In the foregoing embodiment, measurement is performed under an illumination condition including diffused illumination light and an intensive illumination light beam in the direction of −8° to provide the weighting factors for a reflectance of SCI spectral reflection using the first to sixth reference samples SP1 to SP6. However, it may be possible to provide weighting factors (first weighting factors $g_1$, $h_1$) for a reflectance of SCE spectral reflection including diffused illumination light and excluding an intensive illumination light beam in the direction of −8° using the first to sixth reference samples SP1 to SP6.

(2) Further, the second illuminating system 20 may be omitted. In such a case, only first weighting factors $g_1$, $h_1$ for the first illuminating system 10 may be stored in the storage unit 51, and Equation (7) derived from the measurement principle where $x=g_1$, $y=h_1$ may be used. This modified measuring apparatus, although being simpler in construction, can provide interchangeable measurement data eliminating the influence of second illumination.

(3) It may be appreciated to make and store in advance a table containing a number of reflectances which are calculated in accordance with Equation (12) based on varied spectral data and calibration coefficients k, and already calculated first weighting factors $g_1$, $h_1$ and second weighting factors $g_2$, $h_2$. In this case, upon receiving spectral data from the sample spectrometer 30 and the monitoring spectrometer 40, the calculator 53 calculates a reflectance based on the stored table. This measuring apparatus can provide a reflectance of a sample in a shorter time.

(4) The number of reference samples used for determination of first weighting factors $g_1$, $h_1$, and second weighting factors $g_2$, $h_2$ is not limited to six. The weighting factors may be calculated based on four or more reference samples as long as the reflectance and the surface state of samples differ from one another and their respective reflectances are known.

(5) Illuminating systems similar to the illuminators 110 and 120 shown in FIG. 5 may be adopted instead of the first and second illuminating systems 10 and 20. Specifically, one illuminating system first illuminates an areas near to the sample aperture 2, thereby illuminating a sample 3 with diffuse illumination light including light rays incident upon the sample surface at a smaller angle. The other illuminating system first illuminates areas opposite to the sample aperture 2, thereby illuminating the sample with diffuse illumination light including light rays incident upon the sample surface at a larger angle or an angle close to a right angle. In this modification, the sample is illuminated with different light distributions, similar to the foregoing embodiment. Accordingly, the difference between individual measuring apparatus that is caused by second illumination can be eliminated.

Although the present invention has been fully described by way of example with reference to the accompanying drawings, it is to be understood that various changes and modifications will be apparent to those skilled in the art. Therefore, unless otherwise such changes and modifications depart from the scope of the present invention, they should be construed as being included therein.

What is claimed is:

1. A reflection characteristic measuring apparatus comprising:

an integrating sphere formed with an illumination aperture, a sample aperture, and a reception aperture;

an illuminator which supplies illumination light into the integrating sphere through the illumination aperture;

a light receptor which receives light reflected from a sample placed at the sample aperture through the reception aperture to generate light reception data;

an apparent reflectance calculator which calculates an apparent reflectance of the sample based on the generated light reception data;

a storage unit which stores coefficients for rendering a linear combination of an apparent reflectance and N-th power (N is 2 or more integer) of the apparent reflectance closer to a true reflectance of the sample under a given illumination condition; and a true reflectance calculator which calculates a true reflectance of the sample under the given illumination condition by multiplying the terms of the linear combination of an apparent reflectance and N-th power (N is 2 or more integer) of the apparent reflectance by the coefficients stored in the storage unit, respectively.

2. A reflection characteristic measuring apparatus according to claim 1, wherein the light receptor has a reception optical axis extending in a direction inclined substantially 8 degrees with respect to a normal line to a surface of a sample.

3. A reflection characteristic measuring apparatus according to claim 1, wherein:

the integrating sphere is formed with a plurality of illumination apertures in different portions of thereof; and the illuminator includes a plurality of light sources provided at the plurality of illumination apertures, respectively, the plurality of light sources having different light distribution performances.

4. A reflection characteristic measuring apparatus according to claim 3, wherein the plurality of light sources include:

a first light source which illuminates a specified portion of an inner surface of the integrating sphere; and a second light source which illuminates an sample at an incident direction symmetrical to a reception optical axis of the light receptor with respect to a normal line to a surface of a sample.

5. A reflection characteristic measuring apparatus according to claim 4, wherein:

the apparent reflectance calculator calculates a first apparent reflectance of an sample under the illumination of the first light source and a second apparent reflectance of the sample under the illumination of the second light source;

the storage unit stores coefficients for rendering a linear combination of each of the first and second apparent reflectances and N-th power (N is 2 or more integer) of the each of the first and second apparent reflectances closer to a true reflectance of the sample under a given illumination condition; and the true reflectance calculator calculates a true reflectance of the sample under the given illumination condition by multiplying the terms of the linear combination of each of the first and second apparent reflectances and N-th power (N is 2 or more integer) of the each of the first and second apparent reflectances by the coefficients stored in the storage unit, respectively.

6. A reflection characteristic measuring apparatus according to claim 5, wherein the true reflectance calculator calculates a true reflectance of a sample under a given illumination condition in accordance with the following equation:

$$r = k \cdot (g_1 \cdot R_1 + h_1 \cdot R_1^2 + g_2 \cdot R_2 + h_2 \cdot R_2^2)$$

wherein r denotes a true reflectance of the sample under a given illumination condition, $R_1$ denotes a first apparent reflectance, $R_2$ denotes a second apparent reflectance, $g_1$, $h_1$, $g_2$, and $h_2$ denote coefficients for their corresponding terms, and k denotes a calibration coefficient.

7. A reflection characteristic measuring apparatus according to claim 6, wherein the calibration coefficient is stored in the storage unit, the calibration coefficient being determined so as to render an apparent reflectance of a predetermined white reference sample having a known reference reflectance agree with the known reference reflectance.

8. A reflection characteristic measuring apparatus according to claim 1, wherein the coefficients are determined by measuring reflectances of a plurality of reference samples having known true reflectances under a given illumination condition, and comparing the measured reflectances with the known true reflectances, respectively.

9. A reflection characteristic measuring apparatus according to claim 1, wherein the illuminator includes a xenon flash lamp.

10. A reflection characteristic measuring apparatus comprising:

an integrating sphere formed with a first illumination aperture, a second illumination aperture, a sample aperture, and a reception aperture;

a first illuminator which is provided at the first illumination aperture, and supplies a first kind of illumination light into the integrating sphere;

a second illuminator which is provided at the second illumination aperture, and supplies a second kind of illumination light into the integrating sphere, the second kind of illumination light having a different light distribution from the first kind of illumination light;

a light receptor which receives light reflected from a sample placed at the sample aperture through the reception aperture to generate light reception data;

an apparent reflectance calculator calculates a first apparent reflectance of the sample under the first kind of illumination light and a second apparent reflectance of the sample under the second kind of illumination light;

a storage unit which stores a plurality of predetermined weighting factors; and a true reflectance calculator which calculates a true reflectance of the sample under a given illumination condition by multiplying each of the first apparent reflectance, the second apparent reflectance, N-th power (N is 2 or more integer) of the first apparent reflectance, and N-th power (N is 2 or more integer) of the second apparent reflectance by their corresponding weighting factors stored in the storage unit, and adding their respective products to one another.

11. A reflection characteristic measuring apparatus according to claim 10, wherein the light receptor has a reception optical axis extending in a direction inclined substantially 8 degrees with respect to a normal line to a surface of a sample.

12. A reflection characteristic measuring apparatus according to claim 10, wherein:

the first illuminator illuminates a specified portion of an inner surface of the integrating sphere; and the second illuminator illuminates an sample at an incident direction symmetrical to a reception optical axis of the light receptor with respect to a normal line to a surface of a sample.

13. A reflection characteristic measuring apparatus according to claim 10, wherein the true reflectance calculator calculates a true reflectance of a sample under a given illumination condition in accordance with the following equation:

$$r = k \cdot (g_1 \cdot R_1 + h_1 \cdot R_1^2 + g_2 \cdot R_2 + h_2 \cdot R_2^2)$$

wherein r denotes a true reflectance of the sample under a given illumination condition, $R_1$ denotes a first apparent reflectance, $R_2$ denotes a second apparent reflectance, $g_1$, $h_1$, $g_2$, and $h_2$ denote weighting factors for their corresponding terms, and k denotes a calibration coefficient.

14. A method for measuring a reflection characteristic of a sample using an integrating sphere, the method comprising the steps:

measuring an apparent reflectance of a reference sample by using integrating sphere, the reference sample having a known true reflectance under a given illumination condition;

calculating coefficients for rendering a linear combination of a measured apparent reflectance of the reference sample and N-th power (N is 2 or more integer) of the measured apparent reflectance closer to the known true reflectance of the reference sample;

storing calculated coefficients in a storage medium as coefficients for the given illumination condition;

measuring an apparent reflectance of a desired sample by using the integrating sphere;

calculating a true reflectance of the desired sample under the given illumination condition by multiplying the terms of the linear combination of an measured apparent reflectance of the desired sample and N-th power (N is 2 or more integer) of the measured apparent reflectance of the desired sample by the coefficients stored in the storage medium, respectively.

15. A method for measuring a reflection characteristic of a sample using an integrating sphere, the method comprising the steps:

measuring a first apparent reflectance and a second apparent reflectance of a reference sample by using integrating sphere, the reference sample having a known true reflectance under a given illumination condition, the first apparent reflectance being measured under a first kind of illumination light, and the second apparent reflectance being measured under a second kind of illumination light;

calculating coefficients for rendering a linear combination of a measured first apparent reflectance of the reference sample, N-th power (N is 2 or more integer) of the measured first apparent reflectance of the reference sample, a measured second apparent reflectance of the reference sample, and N-th power (N is 2 or more integer) of the measured second apparent reflectance of the reference sample closer to the known true reflectance of the reference sample;

storing calculated coefficients in a storage medium as weighting factors for the given illumination condition;

measuring a first apparent reflectance and a second apparent reflectance of a desired sample by using the integrating sphere, the first apparent reflectance being measured under the first kind of illumination light, and the second apparent reflectance being measured under the second kind of illumination light;

calculating a true reflectance of the desired sample under the given illumination condition by multiplying the terms of the linear combination of a measured first apparent reflectance of the desired sample, N-th power (N is 2 or more integer) of the measured first apparent reflectance of the desired sample, a measured second apparent reflectance of the desired sample, and N-th power (N is 2 or more integer) of the measured second apparent reflectance of the desired sample by the weighting factors stored in the storage medium, respectively.

* * * * *